(12) United States Patent
Fourt et al.

(10) Patent No.: US 10,118,001 B2
(45) Date of Patent: Nov. 6, 2018

(54) RIGID NEEDLE SHIELD GRIPPING CAP ASSEMBLY

(71) Applicant: Eli Lilly and Company, Indianapolis, IN (US)

(72) Inventors: Jesse Arnold Fourt, Menlo Park, CA (US); James R. Yurchenco, Palo Alto, CA (US); Remy O'Leary Pieron, San Francisco, CA (US)

(73) Assignee: Eli Lilly and Company, Indianapolis, IN (US)

( * ) Notice: Subject to any disclaimer, the term of this patent is extended or adjusted under 35 U.S.C. 154(b) by 281 days.

(21) Appl. No.: 15/114,873

(22) PCT Filed: Feb. 6, 2015

(86) PCT No.: PCT/US2015/014733
§ 371 (c)(1),
(2) Date: Jul. 28, 2016

(87) PCT Pub. No.: WO2015/123096
PCT Pub. Date: Aug. 20, 2015

(65) Prior Publication Data
US 2017/0259008 A1 Sep. 14, 2017

Related U.S. Application Data

(60) Provisional application No. 61/938,219, filed on Feb. 11, 2014.

(51) Int. Cl.
*A61M 5/32* (2006.01)
*A61M 5/20* (2006.01)

(52) U.S. Cl.
CPC ......... *A61M 5/3204* (2013.01); *A61M 5/2033* (2013.01); *A61M 5/3202* (2013.01);
(Continued)

(58) Field of Classification Search
CPC .................. A61M 5/3202; A61M 5/3204
See application file for complete search history.

(56) References Cited

U.S. PATENT DOCUMENTS

| 7,195,623 B2 | 3/2007 | Burroughs et al. |
| 8,409,138 B2 | 4/2013 | James et al. |

(Continued)

FOREIGN PATENT DOCUMENTS

| JP | 2012-529322 | 11/2012 |
| WO | 2007047200 | 4/2007 |

(Continued)

OTHER PUBLICATIONS

Stelmi Rigid Needle Shields Patented Anti Pop-Off Design web page found on Dec. 4, 2013 at http://www.stelmi.com/uk/produits/formes_b03.html.

(Continued)

*Primary Examiner* — Laura A Bouchelle
(74) *Attorney, Agent, or Firm* — Marion Daniel Spillman (57) ABSTRACT

A cap assembly mountable to a rigid shield around a needle of a syringe. The cap assembly includes a gripper component and a base cap. The gripper component includes a support frame and a liner that is deformable when sandwiched between the support frame and the rigid shield. When the base cap is installed to the gripper component during manufacture, and with the rigid shield disposed in a bore of the gripper component in any rotational orientation relative thereto, the liner is held by the support frame so as to be deformed against and grip the rigid shield for shield removal purposes so as to allow for removal of the rigid shield from around the needle.

9 Claims, 10 Drawing Sheets

(52) U.S. Cl.
CPC .............. *A61M 2005/206* (2013.01); *A61M 2005/2073* (2013.01)

(56) References Cited

U.S. PATENT DOCUMENTS

| | | |
|---|---|---|
| 2012/0191047 A1 | 7/2012 | Raday et al. |
| 2014/0243753 A1* | 8/2014 | Bostrom ............. A61M 5/3202 604/198 |

FOREIGN PATENT DOCUMENTS

| | | |
|---|---|---|
| WO | 2009040603 | 4/2009 |
| WO | 2010091522 | 8/2010 |
| WO | 2010104779 | 9/2010 |
| WO | 2011101379 | 8/2011 |
| WO | 2011109205 | 9/2011 |
| WO | 2012164397 | 12/2012 |
| WO | 2014154498 | 10/2014 |

OTHER PUBLICATIONS

Patent Cooperation Treaty International Search Report and Written Opinion of the International Searching Authority, pertaining to International Application No. PCT/US2015/014733; dated Mar. 25, 2015.

\* cited by examiner

RIGID NEEDLE SHIELD GRIPPING CAP ASSEMBLY

BACKGROUND OF THE INVENTION

The present invention pertains to pharmaceutical injection devices, and, in particular, to a cap assembly for removing a rigid shield that protects a needle of a syringe.

Many automatic injector devices include a cap feature which when removed from the device removes a protective shield from a needle of the syringe of the device. The protective shield may consist of a multipart construction including an inner shield and an outer shield which are operatively connected together. The inner shield is relatively flexible or elastomeric and provides a sterile barrier around the needle and forms a seal with, for example, the syringe hub from which the needle extends. The inner shield also may seal the tip of the needle such as in designs where the needle is already in fluid communication with the syringe contents. The outer shield is made of a relatively rigid material and protectively surrounds and engages the inner shield. A pulling of the outer or rigid needle shield from the syringe pulls off the inner shield as well.

The cap feature of the device grips the rigid needle shield and serves to make easier the removal of the shield. The cap feature may be larger in diameter than the protective shield, or provided with a mechanical advantage to aid its removal, so as to be more readily grasped and removed by certain users than if the protective shield was removed alone. When the cap feature is removed from the device, which removal removes the protective shield as well due to the cap gripping the rigid needle shield, the needle is uncovered, although frequently still housed within the device prior to being extended therefrom during use, and ready for an injection.

One known cap feature that grips a rigid needle shield utilizes a two-piece assembly. The first piece includes a plastic cup with a tubular portion designed to fit over a rigid needle shield portion of a protective shield previously mounted to an injection needle. The second piece includes a larger diameter, rigid plastic base cap having a softer, grippable periphery that may be provided via a comolding or two shot molding process. Two openings formed through sides of the tubular portion of the plastic cup define a pair of diametrically opposed grip fingers that are resilient so as to be deflectable. Each finger has an inner surface with serrated ribs, and an outer surface with a ramp formed thereon. After the plastic cup is placed onto the rigid needle shield such that the serrated ribs of the resilient fingers are in angular alignment with detents on the rigid needle shield with which they cooperate, the base cap is mounted to the plastic cup so that the tubular portion of the cup inserts into a cavity of the base cap. During this insertion, the base cap interior surface that defines its cavity engages the ramps of the grip fingers to deflect the fingers inward such that the serrated ribs come into gripping contact with the rigid needle shield. The base cap is so mounted until its radial protruding tabs within the base of the cavity snap fit into an annular recess on the exterior of the cup tubular portion, thereby locking the base cap and the plastic cup together to allow them to function as a unit.

While such cap assemblies for removing rigid needle shields may provide a benefit to users, these cap assemblies may complicate the manufacture process. For example, mounting the cap assemblies requires a rotational orientation step to ensure the parts of the rigid needle shield and the cup which cooperate are angularly aligned. Such requires consideration during the manufacturing process, and if unsuccessfully performed may result in an unsatisfactory gripping of the rigid needle shield.

Thus, it would be desirable to provide cap assembly that can overcome one or more of these and other shortcomings of the prior art.

BRIEF SUMMARY OF THE INVENTION

In one form thereof, the present invention provides a cap assembly mountable to a rigid shield around a needle of a syringe, the cap assembly including a gripper component and a base cap. The gripper component is for directly engaging the rigid shield. The gripper component includes a support frame and a liner. The support frame defines an interior hollow. The liner is secured to the support frame within the interior hollow to provide a gripping section that defines a bore sized to axially receive the rigid shield. The liner is formed of a material that is resilient relative to a material forming the support frame and is deformable when sandwiched between the support frame and the rigid shield. The base cap is grippable by a user and includes a body having a surface defining a cavity for accommodating the gripper component. The body surface is configured to compress the gripper component from a first arrangement to a second arrangement when the gripper component inserts within the cavity during manufacture. The liner, when the gripper component is disposed in the first arrangement, does not grip for shield removal purposes the rigid shield when disposed in the bore. The liner, when the gripper component is disposed in the second arrangement with the rigid shield disposed in the bore in any rotational orientation relative thereto, is held by the support frame so as to be deformed against and grip the rigid shield for shield removal purposes so as to allow for removal of the rigid shield from around the needle.

One advantage of the present invention is that a cap assembly may be provided which can be mounted to a rigid needle shield without the portion that directly engages the rigid needle shield being in a particular angular orientation.

Another advantage of the present invention is that a cap assembly may be provided which can function within a range of axial tolerances at which the rigid needle shield can be presented for gripping.

Another advantage of the present invention is that a cap assembly may be provided which, due to its gripping of a rigid needle shield at a point below a hole in a housing baseplate of a device through which a syringe needle extends, allows that hole in the housing baseplate to be made smaller than it would be if the cap assembly were to protrude into the hole.

BRIEF DESCRIPTION OF THE DRAWINGS

The above-mentioned and other advantages and objects of this invention, and the manner of attaining them, will become more apparent, and the invention itself will be better understood, by reference to the following description of embodiments of the invention taken in conjunction with the accompanying drawings, wherein.

Corresponding reference characters indicate corresponding parts throughout the several views. Although the drawings represent an embodiment of the present invention, the drawings are not necessarily to scale, and certain features may be exaggerated or omitted in some of the drawings in order to better illustrate and explain the present invention.

DETAILED DESCRIPTION OF THE INVENTION

Figure 1:
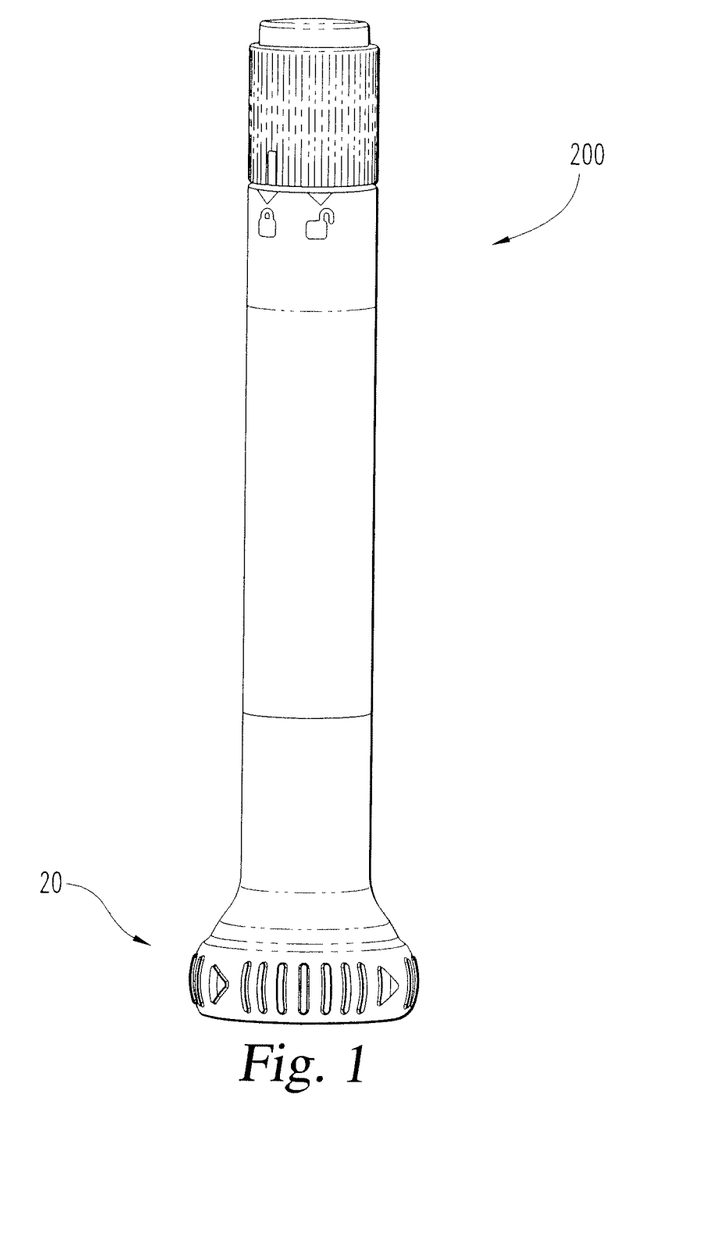
FIG. 1 is a front view of an automatic injection device equipped with a rigid needle shield gripping cap assembly of the present invention.
Figure 2:
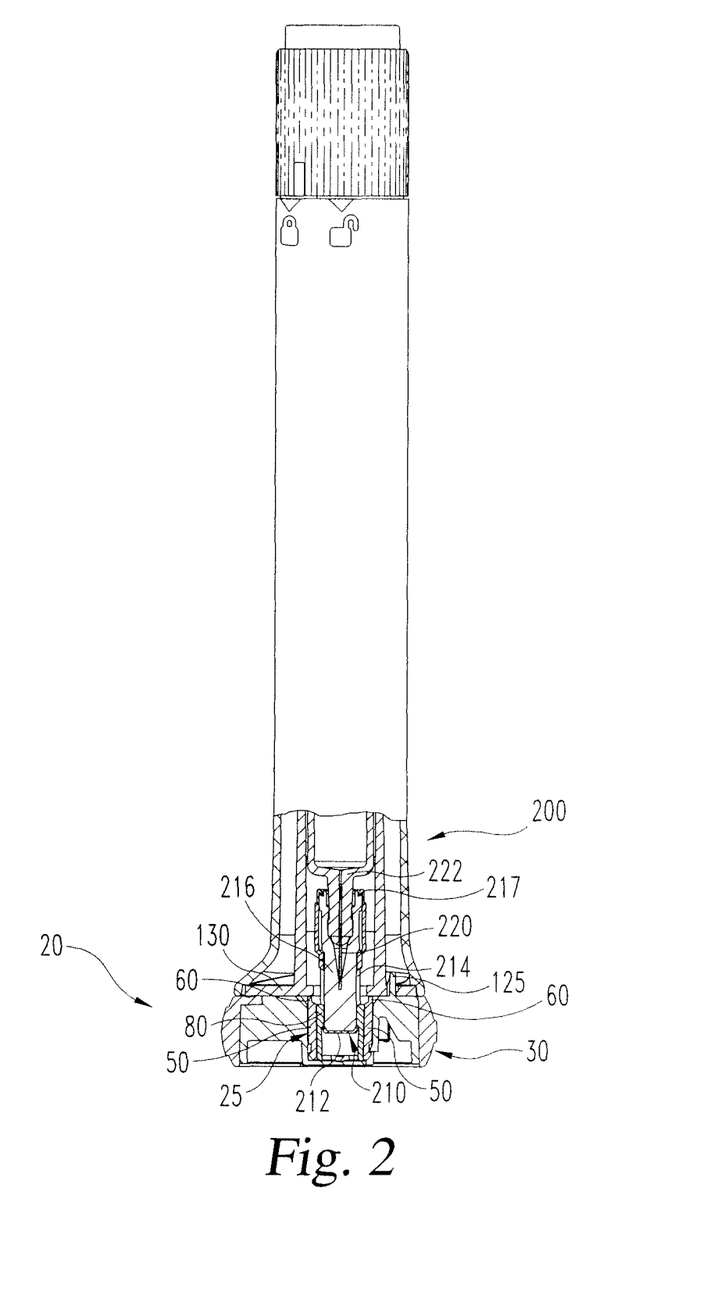
FIG. 2 is a view of the device of FIG. 1 in partial longitudinal cross-section further revealing the cap assembly of the present invention.
Figure 3:
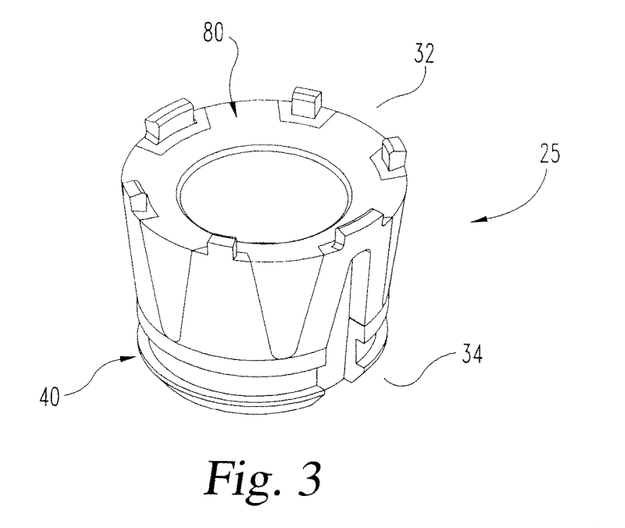
FIG. 3 is a top perspective view of only a completely manufactured gripper component of the cap assembly of the present invention in its neutral state.
Figure 4:
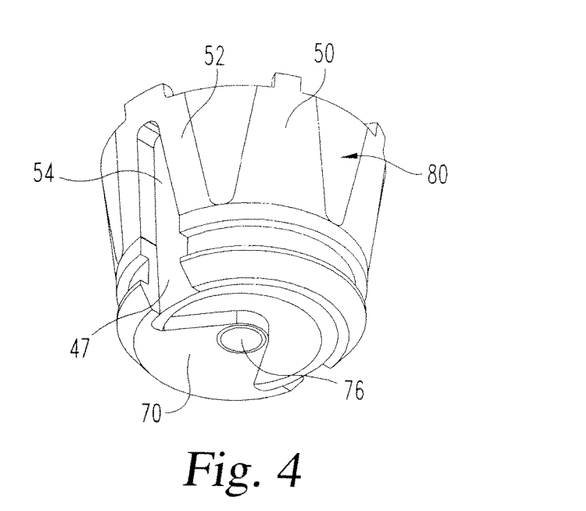
FIG. 4 is a bottom perspective view the gripper component of FIG. 3.
Figure 5:
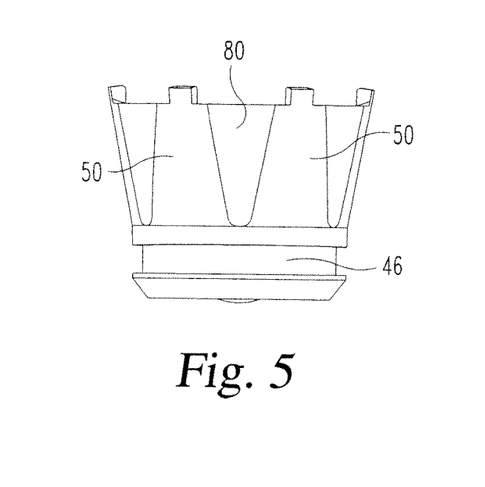
FIG. 5 is a front view of the gripper component of FIG. 3.
Figure 6:
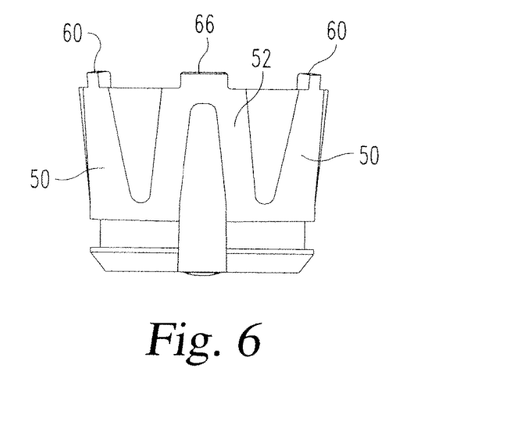
FIG. 6 is a side view of the gripper component of FIG. 3.
Figure 7:
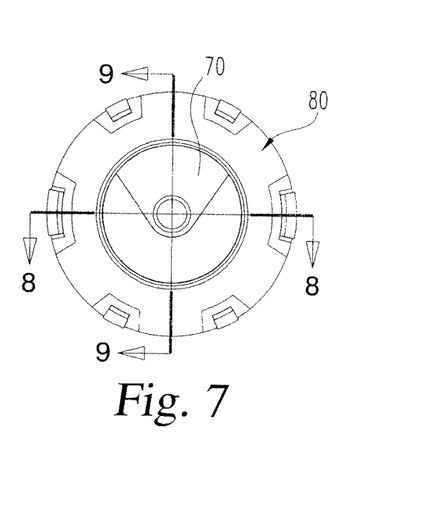
FIG. 7 is a top view of the gripper component of FIG. 3.
Figure 8:
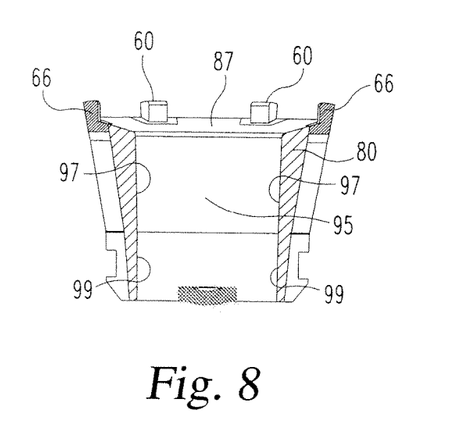
FIG. 8 is a longitudinal cross-sectional view of the gripper component taken along line 8-8 of FIG. 7.
Figure 9:
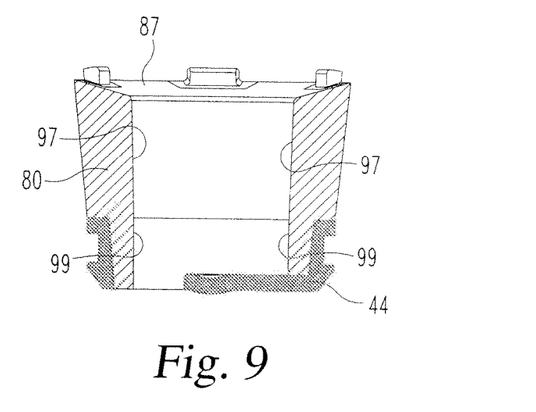
FIG. 9 is a longitudinal cross-sectional view of the gripper component taken along line 9-9 of FIG. 7.
Figure 10:
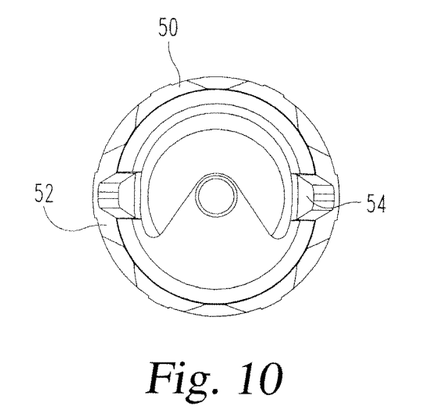
FIG. 10 is a bottom view of the gripper component of FIG. 3.
Figure 11:
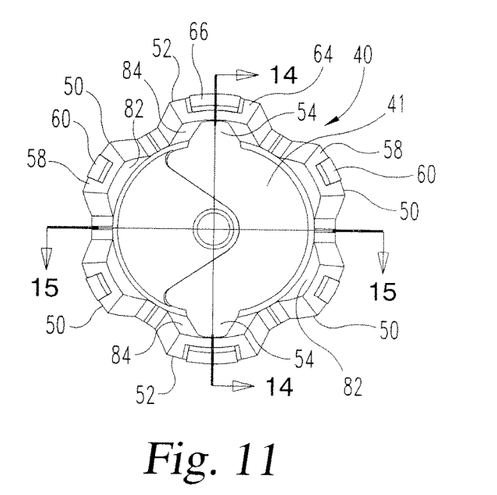
FIG. 11 is a top view of the support frame of the gripper component of FIG. 3 prior to an elastomeric liner being overmolded thereto.
Figure 12:
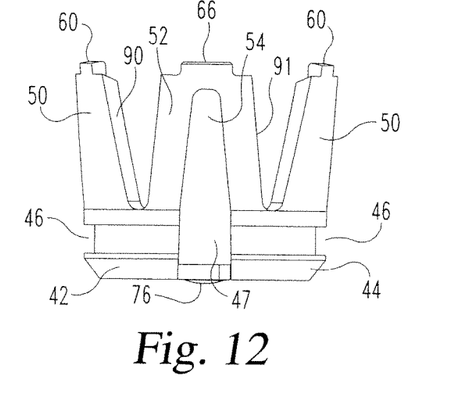
FIG. 12 is a side view of the support frame of FIG. 11.
Figure 13:
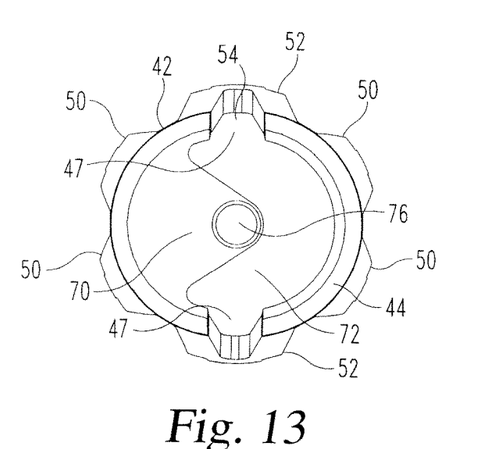
FIG. 13 is a bottom view of the support frame of FIG. 11.
Figure 14:
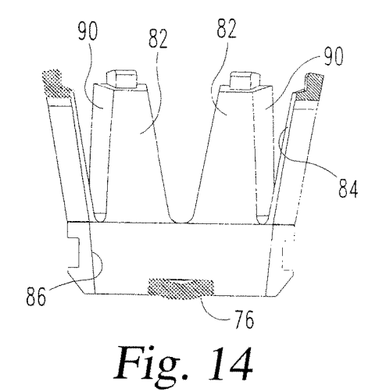
FIG. 14 is a longitudinal cross-sectional view of the support frame taken along line 14-14 of FIG. 11.
Figure 15:
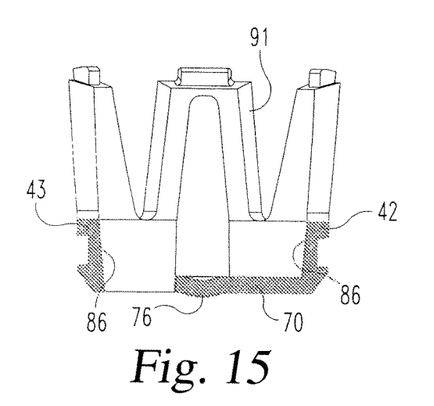
FIG. 15 is a longitudinal cross-sectional view of the support frame taken along line 15-15 of FIG. 11.

In FIGS. 1 and 2, a first embodiment of a cap assembly of the present invention, generally designated 20, is shown mounted to an automatic injection device, generally designated 200. The cap assembly 20 is formed of an inner part or gripper component, generally designated 25, and an outer part or base cap, generally designated 30. Cap assembly 20 serves as a means for gripping a rigid needle shield to allow a user to conveniently remove a needle shield that protectively surrounds a needle 220 of a syringe of device 200 in order to prepare that device for use. Device 200 does not form a part of the present invention, but may be, for example, an automatic injection device as disclosed in PCT international patent application entitled "Trigger Assembly for an Automatic Injection Device", filed with the United States Patent and Trademark Office as Application No. PCT/US2013/064476, the entire disclosure of which is incorporated herein by reference.

With additional reference to FIGS. 3-10, gripper component 25 is shown in its neutral or unstrained state prior to being used with base cap 30 to grip a rigid needle shield.

Gripper component 25 has a cup-like overall shape with a proximal end 32 and a distal end 34. Gripper component 25 is formed from a support frame, generally designated 40, and a liner, generally designated 80, which is comolded with frame 40 within its interior hollow 41.

Support frame 40 is a single piece injection molded out of a relatively rigid and durable material such as glass filled polypropylene. As further shown in FIGS. 11-15, support frame 40 includes a base formed of a pair of diametrically opposed, arc-shaped base sections 42, 44. Each of base sections 42, 44 includes a groove 46 along its outer radial periphery. The opposite ends of base sections 42, 44 are angularly spaced to provide gaps 47. Gaps 47 allow the base sections 42, 44 to be moved closer to each other in situations where forcibly inserted into a bore that is smaller in diameter than the maximum extent of the uncompressed support frame 40.

Base section 42 also includes a lobe 70 protruding radially at its distal end into the circular opening 72 that would otherwise be generally defined by base sections 42, 44. An axially projecting, convex region 76 is formed in lobe 70 at the axial center of the gripper component 25.

Two pairs of solid flanges 50 that are diametrically opposed from each other extend from base sections 42, 44. Another pair of diametrically opposed, apertured flanges 52 also extend from base section 42, 44 between the pairs of solid flanges 50. Each apertured flange 52 is defined by a tapering, interior opening or slot 54 and spans opposite ones of the gaps 47. Slots 54 can partially close when base sections 42, 44 are forced inward so as to decrease gaps 47.

For the orientation of gripper component 25 in FIGS. 3-9, flanges 50 and 52 taper in angular extent as they extend upward. Flanges 50 and 52 also splay radially outward as they extend upward so as to circumscribe a larger area whereby proximal end 32 has a larger diametric extent than does distal end 34. Due to their plastic construction and their thinness in the radial direction, flanges 50 and 52 can flex inward when the flanges are cammed inward as described further below.

The end faces 58 of flanges 50 include upstanding tabs 60, and the end faces 64 of apertured flanges 52 include similar but slightly larger tabs 66. Tabs 60 and 66 are set-offs or points of contact with the device housing end plate.

With reference again to FIGS. 3-9, the liner 80 is molded as part of a two shot molding process directly to the support frame 40 out of a material that is relatively resilient or compressible compared to the material of the support frame 40. One suitable material is a thermoplastic elastomer known as Santoprene®. Liner 80 can conform to and frictionally engage the outer radial periphery of the rigid needle shield that it is intended to grip.

The overmolding liner 80 rings completely the inner radial periphery of support frame 40 other than the lobe 70. Liner 80 is not only adhered via its comolding with the inner radial surfaces 82, 84 and 86 of flanges 50, flanges 52 and base sections 40, 42 respectively, but also fills the angular space between, and adheres via comolding to, the angular side faces 90, 91 of flanges 50 and 52 respectively. Slots 54 and gaps 47 are not filled by the liner 80 so as to not prevent radial compression of flanges 52 and base sections 42, 44 as described above.

Liner 80 forms a substantially annular shape defining a central throughhole or bore 95. The liner interior surface 97 that forms the bore 95 inward of the flanges 50 and 52 is a gripping section that tapers in diameter as it extends distally. The liner interior surface 99 that forms the bore 95 inward of the base sections 42, 44 has a smaller taper in diameter as it extends distally. The tapering configuration of the bore 95 results in the proximal end of the bore being larger in diameter than the distal end of the bore, and this configuration, as well as the chamfered proximal end face 87 of liner 80, can facilitate placement of the gripper component 25 over a rigid needle shield.

The tapering of the liner bore diameter results in an angled configuration relative to the axial direction that is less pronounced than the angle at which flanges 50, 52 splay outward such that liner 80 has a radial thickness that is greater at the proximal end than at the distal end.

The bore 95 of liner 80 is dimensioned by the manufacturer in view of the rigid needle shield with which cap assembly 20 will be used. Bore 95 along its axial length is typically slightly larger in diameter than the rigid needle shield such that the gripper component 25, when in its neutral or ready arrangement shown in FIG. 3, can be freely placed over that rigid needle shield, or in other words without any compression of the liner 80 being required. In such case the gripper component 25, before being engaged by the base cap 30 during manufacturing assembly, could be removed easily from the rigid needle shield without potentially disturbing the rigid needle shield and the needle it surrounds. The bore 95 may also be sufficiently smaller in diameter as to require a minimal amount of force against liner 80 be provided by the rigid needle shield when inserted into bore 95, so long as assembly or removal of the gripper component, if such is desired to be done during manufacturing assembly before the base cap 30 is attached, does not disturb the relationship of the needle and needle shield.

The bore 95 of liner 80 is also dimensioned by the manufacturer in view of the camming relationship of the gripper component 25 with the cap assembly 30, such that liner 80, when cap assembly 30 is connected to gripper component 25, is compressed around the rigid needle shield to provide a grip of the rigid needle shield sufficient for it to be able to pull the protective needle shield off the syringe needle when desired.

Figure 16:
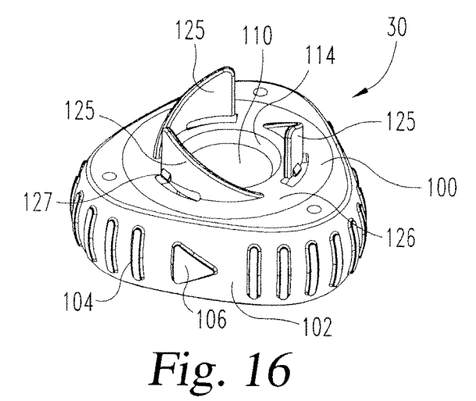
FIG. 16 is a top perspective view of a completely manufactured base cap of the cap assembly of the present invention.
Figure 17:
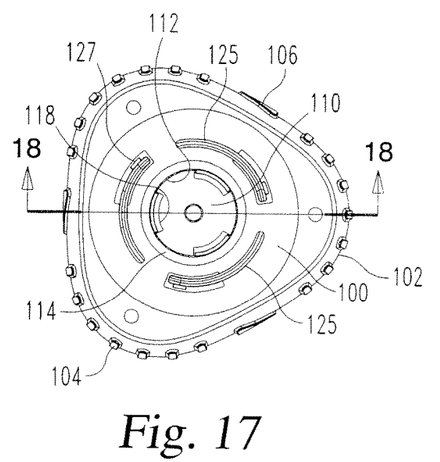
FIG. 17 is a top view of the base cap of FIG. 16.
Figure 18:
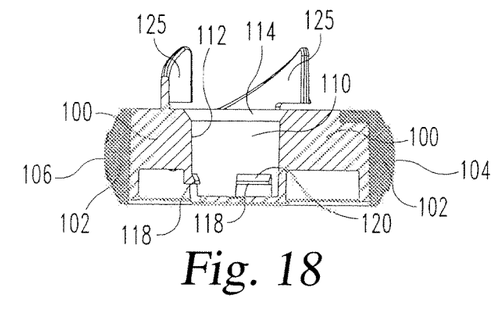
FIG. 18 is a is a longitudinal cross-sectional view of the base cap taken along line 18-18 of FIG. 17.

The cap assembly base cap 30 is further shown in FIGS. 16-18. Base cap 30 is formed of a two shot molding having a central body portion 100 and a gripping periphery 102. Body portion 100 is formed of a rigid material such as polycarbonate. Periphery 102 is molded onto body portion 100 out of a softer material, such as a thermoplastic elastomer such as Santoprene®, and includes knurling 104 to make it easier to grip and directional arrows 106 to show how it can be twisted for removal from the device.

Body portion 100 includes a central cavity 110 defined by a generally cylindrical surface region 112 with a chamfered lead-in surface 114. Surface region 112 is designed to fit around gripping component 25 when placed thereover, but is sized and shaped to bend or cam inward the flanges 50, 52 from the ready arrangement shown in FIGS. 3-10 to a radially compressed, operational arrangement shown in FIG. 2 to create a shield gripping configuration described further below. Three equally angularly spaced tangs 118 inwardly project within cavity 110 near its base. Ramped proximal faces 120 of tangs 118 aid in tangs 118 inserting into groove 46 during the connection of base cap 30 to gripper component 25.

Three cams 125 that are equally angularly spaced around cavity 110 and which are arcuate in shape project upwardly from the proximal surface 126 of body portion 100. Cams 125 fit within arcuate slots 131 provided in the base plate 130 of the device housing show in FIG. 2. A detent 127 provided on each of cams 125 engages base plate 130 to provide a releasable connection of body portion 100 to the base plate to aid in keeping cap assembly 20 on device 200 until its removal as desired. The camming engagement of cams 125 with base plate 130 when a user rotates cap assembly 20 relative to the rest of device 200 in the direction of arrows 106 shifts the cap assembly 20 away from the rest of the device, overcoming the connection of detents 127 with the base plate 130, to facilitate cap removal. The removal of the cap assembly 20 from device 200 may also be done without rotation of the cap assembly but merely by the user pulling it axially.

Figure 19:
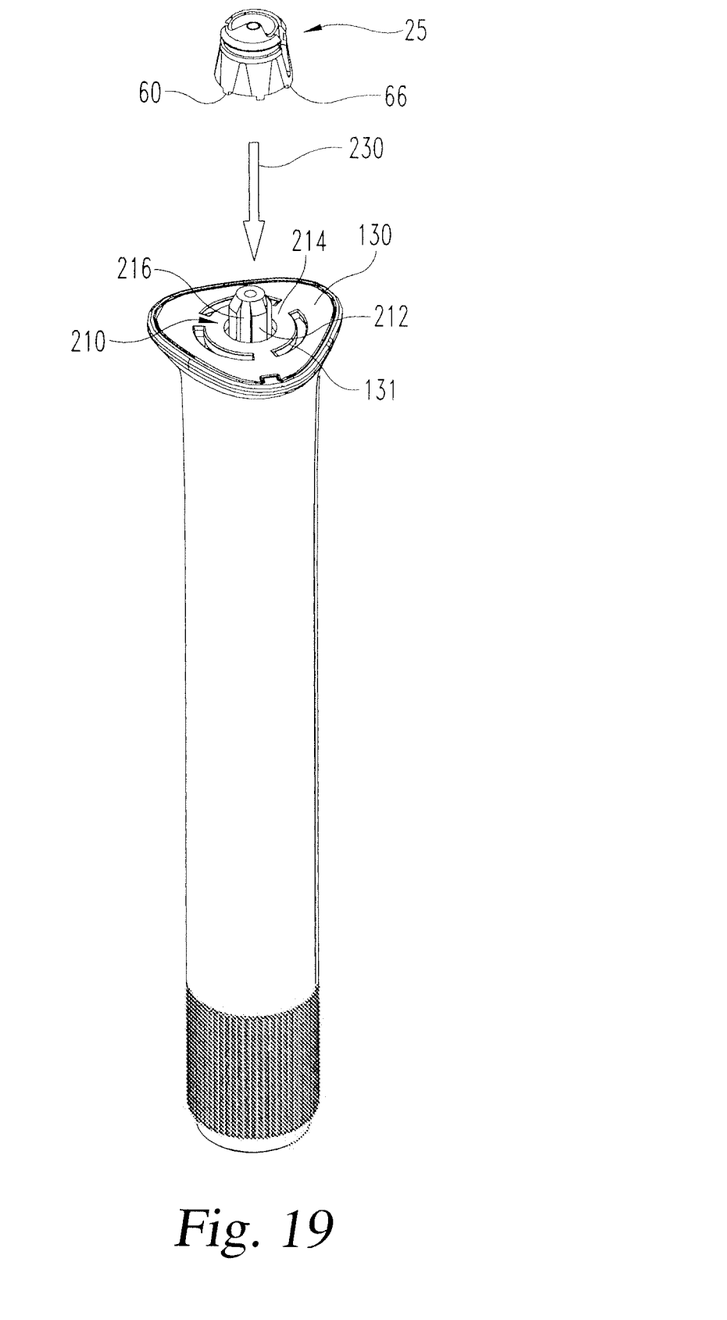
FIG. 19 is perspective view of a step in assembling the inventive cap assembly to a rigid needle shield of an automatic injection device.

The structure of cap assembly 20 will be further understood in view of the following description of its assembly to a device by a manufacturer. In FIG. 19, injection device 200 is shown prepared for the attachment of cap assembly 20 to the rigid needle shield 210 of the device shown projecting beyond base plate 130. The inventive cap assembly can engage rigid needle shields of various shapes known in the art, including those which lack recesses or protrusions that liner 80 can fit into or around. The shown rigid needle shield 210 has a generally cylindrical, projecting end region 212 with longitudinal slots 214 spaced around the circumference through which an elastomeric inner shield 216 is visible. Inner shield 216 seals the end of a needle 220 of a syringe 222 within device 200 as further shown in FIG. 2. Rigid needle shield 210 and inner shield 216 are interconnected at 217 so that the protective shield they provide together around the end of needle 220 is removable as a unit.

Assembly of the cap assembly 20 to rigid needle shield 210 begins with maneuvering a gripper component 25, in its neutral state, into a position axially above the rigid needle shield 210 as shown in FIG. 19, and then moving it down as indicated by arrow 230 such that rigid needle shield 210 inserts into liner bore 95. This insertion ends when the flange offsets 60, 66 abut the base plate 130. While alternatively this insertion could end when the tip of rigid needle shield 210 abuts lobe 70, such is less desired as this transmits forces to the needle shield. Gripper component 25 advantageously need not be in any particular rotational orientation relative to shield 210.

Figure 20:
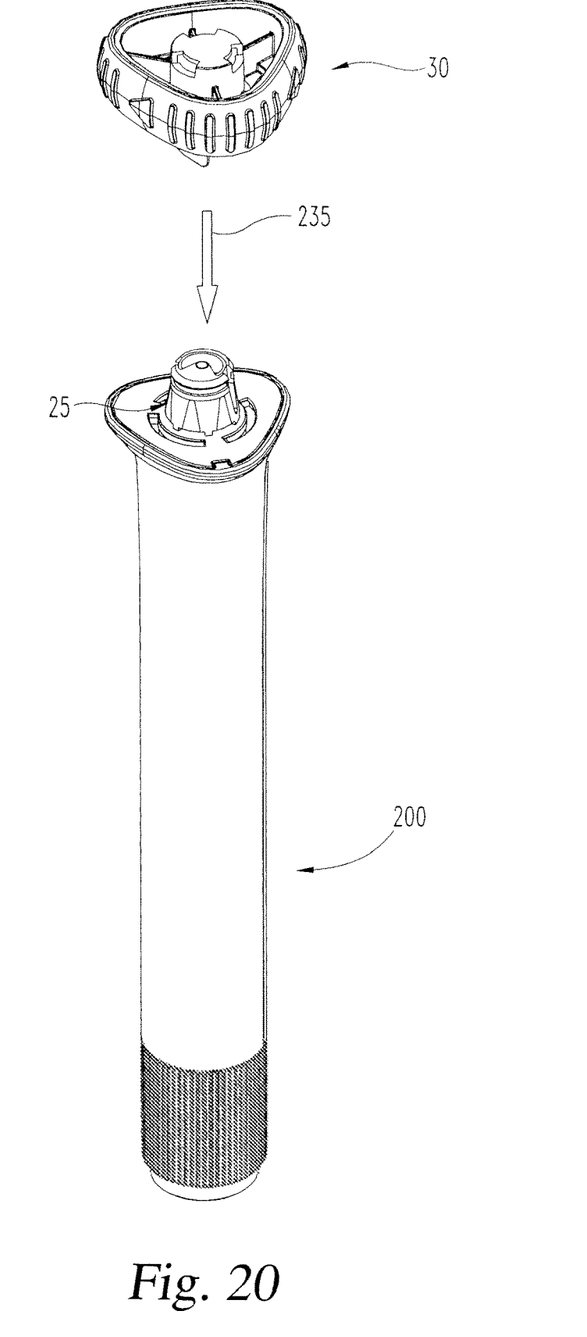
FIG. 20 is perspective view similar to FIG. 19 at a subsequent step.
Figure 21:
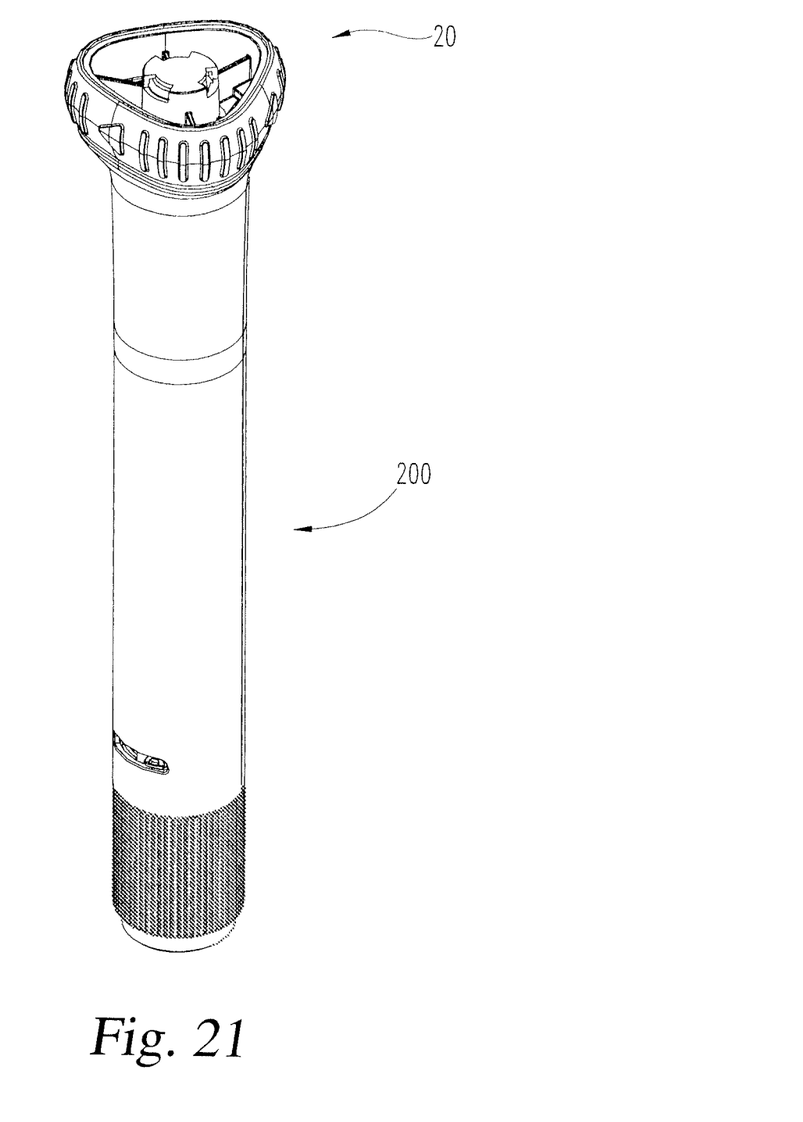
FIG. 21 is perspective view similar to FIG. 20 after the assembly is complete.

Base cap 30 is then brought into a position axially above the gripper component 25 resting over the rigid needle shield 210, and moved down as indicated by arrow 235 in FIG. 20 such that the gripper component 25 inserts within cavity 110 of base cap 30. Initially during this insertion, no resistance is met as the base of gripper component 25 first freely inserts within cavity 110. As the insertion continues, however, cavity surface 112 at chamfered lead-in surface 114 encounters the outer radial peripheries first of base sections 42, 44 and then flanges 50 and 52, which base sections and flanges outwardly extend beyond the diameter of cavity 110. The downward axial movement of base cap 30 causes base sections 42, 44 and flanges 50, 52 to be cammed inward by their engagement with the surface 112, and this camming forces liner 80 against the rigid needle shield 210 so as to be sandwiched between shield 210 and flanges 50 and 52, and between shield 210 and bore surface 112 in the angular spaces between the flanges. When so sandwiched, liner 80 conforms to the periphery of the rigid needle shield 210 to provide a tight grip thereof. The insertion of gripper component 25 is halted after the base cap tangs 118 snap fit into groove 46 of base sections 42, 44, which snap fit ensures that base cap 30 and gripper component 25 are locked together to allow them to function as a unit for shield removal purposes. Frictional forces between surface 112 and the outer periphery of the flanges 50, 52 prevent rotation of the gripper component within base cap 30, but need not so act within the scope of the invention. At this point, cap assembly 20 is securely attached to device 200 as shown in FIG. 21 as well as FIGS. 1 and 2. When the device needle is to have its protective shield removed for use, the cap assembly 20 is simply removed from device 200, which pulls off the gripped rigid needle shield 210 and the inner shield 216 that the rigid needle shield holds.

While this invention has been shown and described as having preferred designs, the present invention may be modified within the spirit and scope of this disclosure. For example, while the liner is described as being overmolded to the support frame as a two part process, the liner could be separately formed and then securely attached to the support frame. This application is therefore intended to cover any variations, uses or adaptations of the invention using its general principles. Further, this application is intended to cover such departures from the present disclosure as come within known or customary practice in the art to which this invention pertains.

We claim:

1. A cap assembly mountable to a rigid shield around a needle of a syringe, said cap assembly comprising:
   a gripper component for directly engaging the rigid shield, said gripper component including a support frame and a liner, said support frame defining an interior hollow, said liner secured to said support frame within said interior hollow to provide a gripping section that defines a bore sized to axially receive the rigid shield, said liner formed of a material that is resilient relative to a material forming said support frame and is deformable when sandwiched between said support frame and the rigid shield; and
   a base cap grippable by a user and comprising a body, said body including a surface defining a cavity for accommodating said gripper component, said body surface configured to compress said gripper component from a first arrangement to a second arrangement when said gripper component inserts within said cavity during manufacture, wherein said liner, when said gripper component is disposed in said first arrangement, does not grip for shield removal purposes the rigid shield when disposed in said bore, and wherein said liner, when said gripper component is disposed in said second arrangement with the rigid shield disposed in said bore in any rotational orientation relative thereto, is held by the support frame so as to be deformed against and grip the rigid shield for shield removal purposes so as to allow for removal of the rigid shield from around the needle.

2. The cap assembly of claim 1 wherein said support frame comprises a base section and a plurality of resilient flanges integrally formed with and extending from said base section, said plurality of flanges in a neutral state splaying radially outward from said base section.

3. The cap assembly of claim 2 wherein said support frame base section comprises a plurality of arc shaped members having ends which are angularly spaced to provide gaps.

4. The cap assembly of claim 3 wherein said flanges include apertured flanges that span said gaps.

5. The cap assembly of claim 1 wherein said liner is comolded with said support frame.

6. The cap assembly of claim 1 wherein said gripping section is annular in shape.

7. The cap assembly of claim 6 wherein said gripping section is adapted to grip an entire circumference of the rigid shield at a common axial position of the rigid shield.

8. The cap assembly of claim 6 wherein said annular gripping section tapers in the radial direction as it extends axially toward a base of said cavity.

9. The cap assembly of claim 1 wherein said gripper component is adapted to directly engage the rigid shield at a point of the rigid shield which projects prior to use beyond a housing of a device holding a syringe on which the rigid shield is mounted.

* * * * *